(12) United States Patent
Berg et al.

(10) Patent No.: US 7,192,984 B2
(45) Date of Patent: Mar. 20, 2007

(54) COMPOSITIONS OF POLYACIDS AND POLYETHERS AND METHODS FOR THEIR USE AS DERMAL FILLERS

(75) Inventors: Richard Berg, Arroyo Grande, CA (US); Samuel Falcone, Morro Bay, CA (US); William G. Oppelt, Arroyo Grande, CA (US); Stephanie M. Cortese, Atascadero, CA (US)

(73) Assignee: Fziomed, Inc., San Luis Obispo, CA (US)

( * ) Notice: Subject to any disclaimer, the term of this patent is extended or adjusted under 35 U.S.C. 154(b) by 0 days.

(21) Appl. No.: 11/189,510

(22) Filed: Jul. 26, 2005

(65) Prior Publication Data

US 2006/0035861 A1    Feb. 16, 2006

Related U.S. Application Data

(60) Continuation-in-part of application No. 10/995,448, filed on Nov. 23, 2004, which is a continuation of application No. 09/023,097, filed on Feb. 13, 1998, now Pat. No. 6,034,140, which is a division of application No. 08/877,649, filed on Jun. 17, 1997, now Pat. No. 5,906,997.

(51) Int. Cl.
| | |
|---|---|
| *C07H 1/00* | (2006.01) |
| *A61K 47/00* | (2006.01) |
| *A61K 31/715* | (2006.01) |
| *A61K 31/727* | (2006.01) |
| *A61K 31/315* | (2006.01) |
| *A61K 31/295* | (2006.01) |
| *A61K 47/32* | (2006.01) |
| *C08G 59/00* | (2006.01) |
| *C08B 11/00* | (2006.01) |
| *C08B 1/00* | (2006.01) |

(52) U.S. Cl. ............. 514/781; 514/54; 514/56; 514/57; 514/494; 514/502; 514/772.4; 536/123.1; 528/403

(58) Field of Classification Search ............ 514/54, 514/56, 494, 781, 502, 772.4, 57; 528/403; 536/43, 56, 98, 123.1
See application file for complete search history.

(56) References Cited

U.S. PATENT DOCUMENTS

| | | | |
|---|---|---|---|
| 3,064,313 A | 11/1962 | Butler | 18/57 |
| 3,328,259 A | 6/1967 | Anderson | 167/84 |
| 3,387,061 A | 6/1968 | Smith et al. | 260/874 |
| 4,024,073 A | 5/1977 | Shimizu et al. | 252/316 |
| 4,141,973 A | 2/1979 | Balazs | 424/180 |
| 4,181,718 A | 1/1980 | Mason et al. | 424/180 |
| 4,442,258 A | 4/1984 | Sumakawa et al. | 524/767 |
| 4,582,640 A | 4/1986 | Smestad et al. | 260/123.7 |
| 4,585,858 A | 4/1986 | Molotsky | 536/401 |
| 4,610,863 A | 9/1986 | Tewari et al. | 423/338 |
| 4,616,644 A | 10/1986 | Saferstein et al. | 128/156 |
| 4,684,558 A | 8/1987 | Keusch et al. | 428/40 |
| 4,713,243 A | 12/1987 | Schiraldi et al. | 424/676 |
| 4,768,523 A | 9/1988 | Cahalan et al. | 128/785 |
| 4,772,419 A | 9/1988 | Malson et al. | 252/315.1 |
| 4,803,075 A | 2/1989 | Wallace et al. | 424/423 |
| 4,853,374 A | 8/1989 | Allen | 514/57 |
| 4,937,254 A | 6/1990 | Sheffield et al. | 514/420 |
| 4,937,270 A | 6/1990 | Hamilton et al. | 514/777 |
| 4,983,585 A | 1/1991 | Pennell et al. | 514/57 |
| 5,017,229 A | 5/1991 | Burns et al. | 106/162 |
| 5,066,709 A | 11/1991 | Chaudhuri et al. | 524/516 |
| 5,068,225 A | 11/1991 | Pennell et al. | 514/57 |
| 5,080,893 A | 1/1992 | Goldberg et al. | 514/57 |
| 5,093,319 A | 3/1992 | Higham et al. | 514/55 |
| 5,140,016 A | 8/1992 | Goldberg et al. | 514/57 |
| 5,156,839 A | 10/1992 | Pennell et al. | 424/78.37 |
| 5,266,326 A | 11/1993 | Barry et al. | 424/423 |
| 5,298,488 A | 3/1994 | Kojima et al. | 514/8 |
| 5,306,500 A | 4/1994 | Rhee et al. | 424/422 |
| 5,324,775 A | 6/1994 | Rhee et al. | 525/54.2 |

(Continued)

FOREIGN PATENT DOCUMENTS

| | | |
|---|---|---|
| EP | 0 138 572 A2 | 4/1985 |
| EP | 0 189 553 A2 | 8/1986 |
| EP | 0 193 510 A1 | 9/1986 |
| EP | 0 265 561 A1 | 10/1986 |
| EP | 0 264 719 A2 | 4/1988 |

(Continued)

OTHER PUBLICATIONS

Elkins, et al., *Adhesion prevention by solutions of sodium carboxymethylcellulose in the rat. I.* Fertility and Sterility, vol. 41, No. 6, 926-928, Jun. 1984.

Chaikof, *Platelet Interaction with Poly(ethylene Oxide) Networks*, AIChE Journal, vol. 36, No. 7, 994-1002, Jul. 1990.

Bottenberg, et al., *Development and Testing of Bioadhesive, Fluoride-containing Slow-release Tablets for Oral Use*, J. Pharm. Pharmacol., 43:457-464, 1991.

Amiji, *Permeability and blood compatibility properties of chitosan-poly(ethylene oxide) blend membranes for haemodialysis*, Biomaterials, 16, 593-599, 1995.

(Continued)

*Primary Examiner*—L. E. Crane
(74) *Attorney, Agent, or Firm*—Fliesler Meyer LLP

(57) ABSTRACT

The present invention relates to improved methods for filling the skin for cosmetic or medical purposes. Compositions comprising carboxymethyl cellulose (CMC), polyethylene oxide (PEO) and calcium ions can be made and have physical properties that depend on the amounts and types of CMC, PEO, and calcium ions to form ioniclaly cross-linked gels. Compositions can be formed into microspheres, coacervates, gels, or membranes. Gels, microspheres and coacervates can be injected directly into a site for dermal filling. Membranes can be surgically introduced, where they swell to form hydrated gels. After introduction, the dermal filler persists for a period of time and then can disintegrate and be removed from the body.

18 Claims, 4 Drawing Sheets

U.S. PATENT DOCUMENTS

| | | | |
|---|---|---|---|
| 5,354,790 A | 10/1994 | Keusch et al. | 523/300 |
| 5,356,883 A | 10/1994 | Kuo et al. | 514/54 |
| 5,374,446 A | 12/1994 | Ferenz et al. | 426/611 |
| 5,376,375 A | 12/1994 | Rhee et al. | 424/423 |
| 5,462,749 A | 10/1995 | Rencher | 424/484 |
| 5,502,081 A | 3/1996 | Kuo et al. | 514/777 |
| 5,532,221 A | 7/1996 | Huang et al. | 514/53 |
| 5,550,178 A | 8/1996 | Desai et al. | 524/56 |
| 5,599,852 A | 2/1997 | Scopelianos et al. | 523/105 |
| 5,621,093 A | 4/1997 | Swann et al. | 536/55.2 |
| 5,681,873 A | 10/1997 | Norton et al. | 523/115 |
| 5,709,854 A | 1/1998 | Griffith-Cima et al. | 424/93.7 |
| 5,711,958 A | 1/1998 | Cohn et al. | 424/423 |
| 5,728,752 A | 3/1998 | Scopelianos et al. | 523/113 |
| 5,800,832 A | 9/1998 | Tapolsky et al. | 424/449 |
| 5,824,333 A | 10/1998 | Scopelianos et al. | 424/423 |
| 5,827,937 A | 10/1998 | Agerup | 536/123.12 |
| 5,874,417 A | 2/1999 | Prestwich et al. | 514/54 |
| 5,874,500 A | 2/1999 | Rhee et al. | 525/54.1 |
| 5,906,997 A | 5/1999 | Schwartz et al. | 514/781 |
| 5,922,025 A | 7/1999 | Hubbard | 623/11 |
| 5,942,253 A | 8/1999 | Gombotz et al. | 424/501 |
| 5,955,096 A | 9/1999 | Santos et al. | 424/434 |
| 5,968,500 A | 10/1999 | Robinson | 424/78.08 |
| 5,985,312 A | 11/1999 | Jacob et al. | 424/434 |
| 6,017,301 A | 1/2000 | Schwartz et al. | 514/781 |
| 6,033,680 A * | 3/2000 | Dixon et al. | 424/401 |
| 6,034,140 A | 3/2000 | Schwartz et al. | 514/781 |
| 6,102,254 A * | 8/2000 | Ross | 222/192 |
| 6,124,273 A | 9/2000 | Drohan et al. | 514/55 |
| 6,129,761 A | 10/2000 | Hubbell | 632/11 |
| 6,133,325 A | 10/2000 | Schwartz | 514/781 |
| 6,187,044 B1 | 2/2001 | Eppley | 623/8 |
| 6,231,613 B1 | 5/2001 | Greff et al. | 623/23.58 |
| 6,277,392 B1 | 8/2001 | Klein | 424/426 |
| 6,284,284 B1 | 9/2001 | Naughton | 424/520 |
| 6,312,725 B1 | 11/2001 | Wallace et al. | 424/484 |
| 6,323,278 B2 | 11/2001 | Rhee et al. | 525/54.1 |
| 6,423,381 B1 * | 7/2002 | Colton et al. | 427/510 |
| 6,432,437 B1 | 8/2002 | Hubbard | 424/424 |
| 6,436,424 B1 | 8/2002 | Vogel et al. | 424/422 |
| 6,458,889 B1 | 10/2002 | Trollsas et al. | 525/54.1 |
| 6,533,819 B1 | 3/2003 | Urry et al. | 623/17.16 |
| 6,534,591 B2 | 3/2003 | Rhee et al. | 525/54.1 |
| 6,537,574 B1 | 3/2003 | Hubbard | 424/484 |
| 6,544,503 B1 | 4/2003 | Vanderhoff et al. | 424/78.17 |
| 6,565,960 B2 | 5/2003 | Koob et al. | 428/304.4 |
| 6,566,345 B2 * | 5/2003 | Miller et al. | 514/54 |
| 6,586,493 B1 | 7/2003 | Massia et al. | 522/87 |
| 6,652,883 B2 | 11/2003 | Goupil et al. | 424/489 |
| 6,660,301 B1 | 12/2003 | Vogel et al. | 424/489 |
| 6,699,294 B2 | 3/2004 | Urry | 623/23.72 |
| 6,869,938 B1 | 3/2005 | Schwartz | 514/57 |
| 6,923,961 B2 * | 8/2005 | Liu et al. | 424/94.64 |
| 2003/0202970 A1 * | 10/2003 | Liu et al. | 424/94.64 |
| 2004/0096422 A1 | 5/2004 | Schwartz | |

FOREIGN PATENT DOCUMENTS

| | | |
|---|---|---|
| EP | 0 581 581 A2 | 2/1994 |
| JP | 9-241973 A | 9/1997 |
| WO | WO 84/03302 | 8/1984 |
| WO | WO 86/00912 | 2/1986 |
| WO | WO 89/02445 | 3/1989 |
| WO | WO 90/10020 | 9/1990 |
| WO | WO 97/01345 | 6/1996 |
| WO | WO 97/23564 | 7/1997 |
| WO | WO 98/58011 | 12/1998 |

OTHER PUBLICATIONS

Gurny, et al., *Bioadhesive intraoral release systems: design, testing and analysis,* Biomaterials, vol. 5, 336-340, 1984.

Kulicke, et al., *Characterization of aqueous carboxymethylcellulose solutions in terms of their molecular structure and its influence on rheological behavior,* Polymer, vol. 37, No. 13, 2723-2731, 1996.

Ohno, et al., *Interpolymer Complex Formation of Polysaccharides with Poly(ethylene oxide) or Poly(1-vinyl-2-pyrrolidone) through Hydrogen Bond,* Makromol. Chem., Rapid Comun., 2, 511-515, 1981.

Didishelm, et al., *Hematologic and Coagulation Studies in Various Animal Species,* J. Lab. & Clin. Med., 866-875, Jun. 1959.

Harris, et al., *Analysis of the Kinetics of peritoneal adhesion formation in the rat and evaluation of potential antiadhesive agents,* Surgery, 663-669, Jun. 1995.

Becker, et al., *Prevention of Postoperative Abdominal Adhesions by a Sodium Hyaluronate-based Bioresorbable Membrane: A Prospective, Randomized, Double-Blind Multicenter Study,* Journal of American College of Surgeons, vol. 183, 297-306, Oct. 1996.

Interceed (TC7) Adhesion Barrier Study Group, *Prevention of postsurgical adhesions by Interceed (TC7), *an absorbable adhesion barrier: a prospective, randomized multicenter clinical study,* Fertility and Sterility, vol. 51, No. 6, 933-938, Jun. 1989.

Diamond, et al., *Reduction of adhesions after uterine myomectomy by Seprafilm * membrane (HAL-F): a blinded, prospective, randomized, multicenter clinical study,* Fertility and Sterility, vol. 66, No. 6, 904-910, Dec. 1996.

Sung, et al., *Swelling properties of hyaluronic acid ester membranes,* Journal of Membrane Science, 92, 157-167, 1994.

*Sepra film™ Bioresorbable Membrane, Product Monograph for the Reduction of Postsurgical Adhesions,* Genzyme Corporation, 1-29, 1996.

Kitano, et al., *Viscous Carboxymethylcellulose in the Prevention of Epidural Scar Formation,* Spine, vol. 16, No. 7, Jul. 1991.

*Hercules Cellulose Gum, Sodium Carboxymethylcellulose, Chemical and Physical Properties,* Hercules, Inc., 1-31, 1984.

Takayma, et al., *Effect of Interpolymer Complex Formation on Bioadhesive Property and Drug Release Phenomenon of Compressed Tablet Consisting of Chitosan and Sodium Hyaluronate,* Chem. Pharm. Bull., 38(7), 1993-1997, 1990.

Aurora, et al., *Pathology of Peritoneal Adhesions—An Experimental Study,* Indian J. Med. Res., 62, 4, 539-544, Apr. 1974.

Harland, et al., *Polyelectrolyte Gels, Properties, Preparation, and Applications,* American Chemical Society Symposium Series, Nov. 11-16, 1990, 480.

Feddersen, et al., *Sodium Carboxymethylcellulose,* Industrial Gums, Polysaccharides and Their Derivatives, Third Edition, 537-579, 1993.

Steizer, et al., *Carboxymethylcellulose,* Handbook of Water-Soluble Gums and ResinsChapter 4, pp. 4-1-4-28, 1980.

Danishefsky, et al., *Conversion of Carboxyl Groups of Mucopolysaccharides into Amides of Amino Acid Esters,* Carbohyd. Res., 16, 199-205, 1971.

Tsuchida, et al., *Interactions Between Macromolecules in Solution and Intermacromolecular Complexes,* Advance Polymer Science, 45-122, 1982.

Anseth, et al., *Mechanical properties of hydrogels and their experimental determination,* Biomaterials, 17, 1647-1657, 1996.

Agrawal, et al., *"Technique to Control pH in Vicinity of Biodegrading PLA-PGA Implants,"* John Wiley & Sons, Inc., 1997, pp. 105-114.

Lenaerts, Ph.D., et al., *"Bioadhesive Drug Delivery Systems,"* CRC Press, Inc., 1990, pp. 25-168.

Elkins, et al., *Adhesion prevention by solutions of sodium carboxymethylcellulose in the rat. II.* Fertility and Sterility, vol. 41, No. 6, 929-932, Jun. 1984.

Arnold W. Klein, MD., et al., *The History of Substances for Soft Tissue Augmentation,* 2000 by the American Society for Dermatologic for Surgery, Inc., Dermatol Surg; 2000:26, pp. 1096-1105.

Rhoda S. Narins, MD., et al., *A Randomized, Double-Blind, Multicenter Comparison of the Efficacy and Tolerability of Restylane Versus Zyplast for the Correction of Nasolabial Folds*, 2003 by the American Society for Dermatologic for Surgery, Inc., Dermatol Surg; 2003:29, pp. 588-595.

Tracey Hotta, BScN, RN, CPSN; *Dermal Fillers the Next Generation*; Plastic Surgical Nursing, Jan.-Mar. 2004, vol. 24, No. 1, pp. 14-19.

* cited by examiner ary purposes. For
COMPOSITIONS OF POLYACIDS AND POLYETHERS AND METHODS FOR THEIR USE AS DERMAL FILLERS

CLAIM OF PRIORITY

This Application is a Continuation-In-Part of U.S. patent application Ser. No. 10/995,448, filed Nov. 23, 2004, titled "Compositions of Polyacids and Polyethers and Methods for Their Use in Reducing Adhesions," Inventors: Herbert B. Schwartz, John M. Blackmore, Stephanie M. Cortese and William G. Oppelt, which is a Continuation of U.S. patent application Ser. No. 09/023,097, filed Feb. 13, 1998, now U.S. Pat. No. 6,034,140, issued Mar. 7, 2000, which is a Division of U.S. patent application Ser. No. 08/877,649, filed Jun. 17, 1997, now U.S. Pat. No. 5,906,997, issued May 25, 1999. The above application and patents are incorporated herein fully by reference.

FIELD OF THE INVENTION

This invention relates generally to the manufacture and use of materials for dermal augmentation comprising carboxypolysaccharide/polyether intermacromolecular complexes, cross-linked gels comprising polyacids, polyalkylene oxides and multivalent ions and the use of those compositions and gels to augment soft tissues.

BACKGROUND OF THE INVENTION

Augmentation of the skin can be an important factor in recovering from injury or for cosmetic purposes. For example, with normal aging, skin may become loose or creases can form, such as nasal-labial folds. In the face, creases or lines may adversely affect a person's self esteem or even a career. Thus, there has been a need for compositions and methods that can diminish the appearance of creases or lines.

Further, there are situations in which loss of tissue can leave an indentation in the skin. For example surgical removal of a dermal cyst, lipoatrophy or solid tumor can result in loss of tissue volume. In other cases, injuries, such as gunshot wounds, knife wounds, or other excavating injures may leave an indentation in the skin. Regardless of the cause, it can be desirable to provide a dermal filler that can increase the volume of tissue to provide a smoother or more even appearance.

Several compositions are available for such purposes. Collagen is often used as an injectable material for soft tissue augmentation. Additionally, numerous other materials, including proteins, fats, hyaluronic acid (HA), polyalcohols, and other polymers have been used as injectable dermal fillers. However, non-cross linked, hydrophilic polymers such as collagen, gelatin and HA have not performed well and must be covalently cross-linked to remain in place to be effective. One example is Zyderm™, which is uncrosslinked bovine collagen, was not effective as a dermal filler unless it was first cross-linked with glutaraldehyde to convert it to Zyplast™. Similarly, HA has not been sufficiently effective as a space filling material when injected or implanted in the body unless it is first cross-linked.

Compositions of CMC and modified CMC have unique properties that allow such compositions to be injected into the skin to fill spaces and to provide support where support is desired. One example for needed support is dermal augmentation in the face where dermal and subdermal volume is lost due to aging. CMC has a unique property of being an elastic gel with unique physical properties such as dynamic, plastic and zero shear viscosity, tissue adhesiveness, cohesiveness and flow characteristics. In addition, it can achieve these properties without the requirement of covalent cross-linking. CMC is particularly unique because chemical modifications of CMC expand the number of physical properties that make it an ideal injectable polymer for human treatment. For example, change in the degree of substitution has a dramatic effect on thixotropy and on viscosity of the gel. Its biocompatability and viscoelastic properties make it uniquely useful for injection into human skin where it becomes a space filling, biocompatible polymer.

Other polymers tested for their ability to perform as space filling gels are polysaccharides that have been used for soft tissue filing are inferior to CMC. For example, HA must be cross-linked to cause it to function as an elastic gel. Cross-linking limits its ability to be injected through narrow gauge needles, because the cross-linking converts HA into particles.

Proteins used for dermal augmentation, such as collagen, also must be cross-linked to perform well as dermal fillers. For example, Zyplast™ is a cross-linked bovine collagen dermal filler.

CMC can be a carrier for additional material for additional material for the skin, including hydrogel polymers such as PEO and emulsions. CMC can be used to deliver drugs to the skin, such as antioxidants, retinol, vitamins and growth factors. Covalent cross-linking of polymers converts them into particles that diminish their ability to deliver additional polymers, liposomes, emulsions or other particulates.

Numerous substances have been tested over the years for augmenting soft tissue in the dermis in the face to improve cosmesis by filling depressions in the skin (Klein and Elson, *The History of Substances for Soft Tissue Augmentation*, Dermatological Surgery 26:1096–1105, 2000). This is an area that continues to be studied as ther is no clearly superior material or product (Hotta, *Dermal Fillers: The Next Generation*, Plastic Surgical Nursing 24(1):14–19, 2004). These fillers are prepared from several polymers including bovine collagen, porcine collagen, chicken or bacteria fermented HA, gelatin, all of which are cross-linked covalently to reduce their dissolution time or immunological reactions. Fillers also include autologous human collagen (cross-linked collagen from the patient), human cadaver dermis (cross-linked human collagen). Additional fillers are those that are insoluble in the dermis, including PMMA beads, dPTFE (expanded polytetrofluoroethylene), poly lactic acid, recombinant elastin, and thermoplastics that form gels when injected into humans (Klein and Elson, *The History of Substances for Soft Tissue Augmentation*, Dermatological Surgery 26:1096–1105, 2000). More recently, ceramic particles (U.S. Pat. No. 5,922,025) and also PMMA microspheres (Lemperle et al, *Migration Studies and Histology of Injectable Microspheres of Different Sizes in Mice*, Plast. Reconstr. Surg 113(5):1380–1390 (2004) have been used for soft tissue augmentation.

Dermal fillers are used to fill scars, depressions and wrinkles. Dermal filler substances have various responses in the dermis from phagocytosis to foreign body reactions depending on the material (Lemperle et al., *Human Histology and Persistence of Various Injectable Filler Substances for Soft Tissue Augmentation*, Aesthetic Plast. Surg. 27(5): 354–366; discussion 367 (2003). One goal of dermal fillers it to temporarily augment the dermis to correct the surface contour of the skin without producing an unacceptable inflammatory reaction, hypersensitivity reaction or foreign body reaction that causes pain, redness or excessive scar formation for a period of time.

One of the first materials to be used for dermal augmentation is Zyplast™ derived form bovine collagen. A newer material used for this application is Restylane™ derived from bacteria-produced HA. Because challenges include both biocompatibility and persistence in the skin, new dermal fillers are compared to one of the existing products such as Zyplast™ or Restylane™ (Narins et al., *A Randomized, Double-Blind, Multicenter Comparison of the Efficacy and Tolerabiliyt of Restylane Versus Zyplast for the Correction of Nasolabial Folds*, Dermatol. Surg. 29:588–595(2003). However, there is a need for better compositions for use as dermal fillers.

SUMMARY OF THE INVENTION

To achieve these and other objectives, certain embodiments of the instant invention include use of carboxymethyl cellulose (CMC), polyethylene oxide (PEO) and calcium ions to prepare an ionically cross-linked composition for use as dermal filler. The materials that perform well for dermal augmentation behave Theologically as elastic gels at all frequencies. That is, for the frequency spectrum from 0.01 Hz to 100 Hz, the elastic modulus is higher than the viscous modules and therefore, the material remains a gel at all deformation rates. For non-cross-linked HA products, the elastic and viscous moduli crossover at some frequency and stress. At frequencies lower than this transition point, the materials are predominately viscous fluids that do not act as space filling gels.

In contrast, gels that are based on CMC are elastic materials over the entire frequency range and do not have a crossover point. Therefore, these materials behave rheologically the same as cross-linked hydrogels and work very well as space filling materials for dermal augmentation. In contrast with covalently cross-linked materials, however, CMC-based gels to not have to be chemically cross-linked and can be formulated with more consistency than covalently cross-linked materials. In addition, chemical cross-linking generally produces some unwanted side products and impurities in the polymer matrix that can be harmful in not completely removed from the formulation.

One type of CMC and PEO containing materials is Oxiplex®, whose composition and methods for manufacture are described in U.S. Pat. No. 6,869,938. Oxiplex® polymers have been extensively used as surgical implants and have excellent biocompatibility in both animal studies and clinical experience. Unique properties of Oxiplex® make it superior in terms of biocompatibility to many other biomaterials such as polyesters, hyaluronan, collagen and fibrin. It is synthetic, not derived from animal sources and is non-inflammatory. Collagen and HA are derived from animal or bacterial by-products, and may provoke a complicating inflammatory or immune responses in some patients. They are expensive to manufacture because they must be extracted from biological sources. Other biomaterials require multi-step mixing before use or cannot be used in minimally invasive procedures.

BRIEF DESCRIPTION OF THE FIGURES

Aspects of this invention are described with reference to specific embodiments thereof. Other features of aspects of this invention can be appreciated with reference to the Figures, in which.

DETAILED DESCRIPTION

Figure 1:
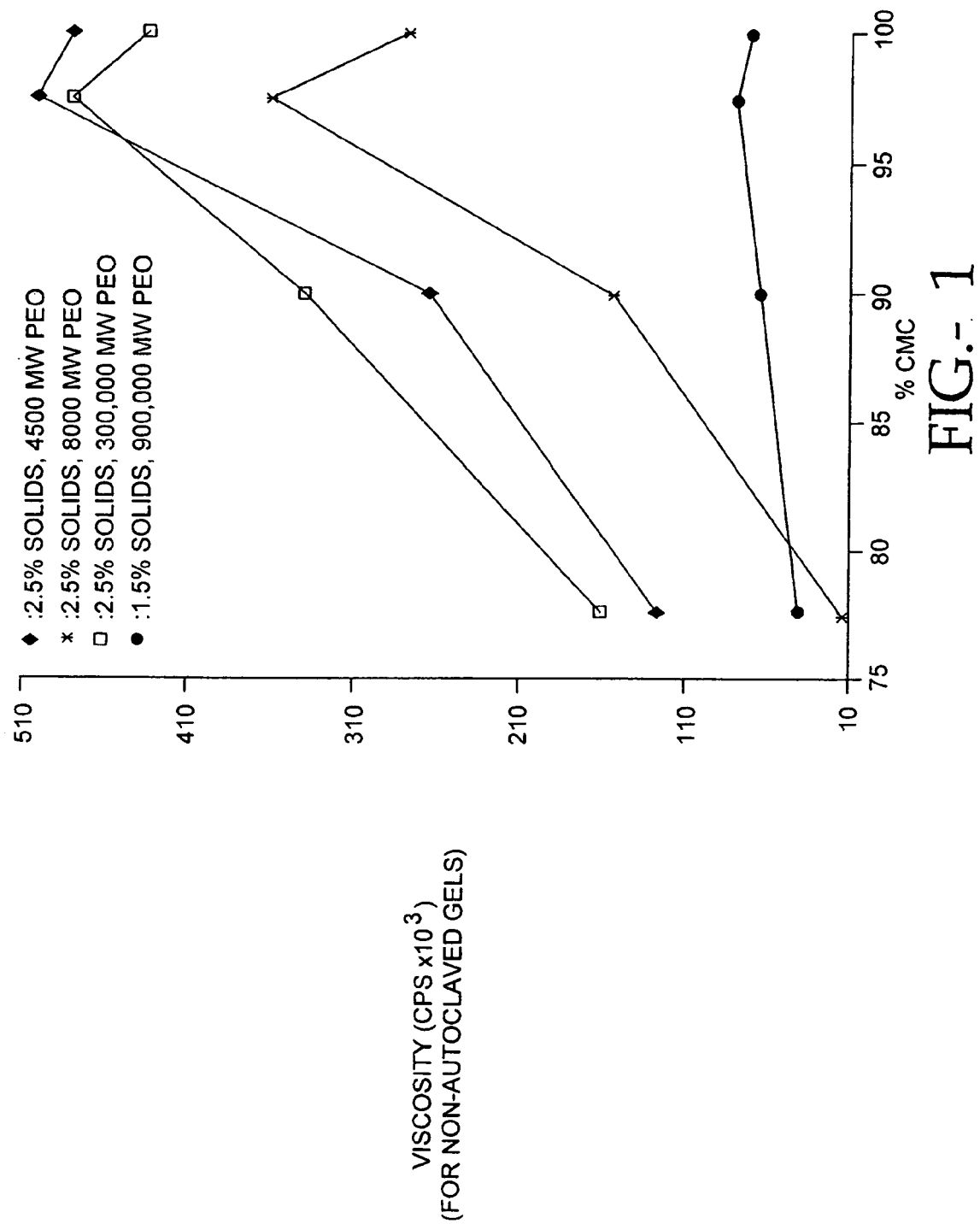
FIG. 1 depicts the relationships between CMC/PEO ratio, molecular weight of PEO and total solids composition on the viscosity of ionically cross-linked gels according to one embodiment of this invention.

Definitions:

Before describing the invention in detail, the following terms are defined as used herein.

The term "association complex" or "intermacromolecular complex" means the molecular network formed between polymers containing CPS, polyacids, PE, polyalkylene oxide and/or multivalent ions, wherein the network is cross-linked through hydrogen and/or ionic bonds.

The term "bioadhesive" means being capable of adhering to living tissue.

The term "bioresorbable" means being capable of being reabsorbed and eliminated from the body.

The term "biocompatible" means being physiologically acceptable to a living tissue and organism.

The term "carboxymethylcellulose" ("CMC") means a polymer composed of repeating carboxylated cellobiose units, further composed of two anhydroglucose units (β-glucopyranose residues), joined by 1,4 glucosidic linkages. The cellobiose units are variably carboxylated.

The term "carboxypolysaccharide" ("CPS") means a polymer composed of repeating units of one or more monosaccharides, and wherein at least one of the monosaccharide units has a hydroxyl residue substituted with a carboxyl residue.

The term "chemical gel" means a gel network comprised of covalently cross-linked polymers.

The term "degree of substitution" ("d.s.") means the average number of carboxyl or other anionic residues present per mole of cellobiose or other polymer.

The term "gel pH" means the pH of the gel or the pH of the casting solution from which the gel or a partially dried form of the gel is formed.

The term "hyaluronic acid" ("HA") means an anionic polysaccharide composed of repeat disaccharide units of N-acetylglucosamine and glucuronic acid. HA is a natural component of the extracellular matrix in connective tissue.

The term "hydration" (also "swelling") means the process of taking up solvent by a polymer solution.

The term "hydration ratio" (also "swelling ratio") means the wet weight of a hydrated membrane, sponge or microsphere less the dry weight divided by the dry weight X 100%.

The term "hydrogel" means a three-dimensional network of hydrophilic polymers in which a large amount of water is present.

The terms "physical gel," "physical network" and "pseudo gel" mean non-covalently cross-linked polymer networks wherein the association of polymers in these gels is characterized by relatively weak and potentially reversible chain-chain interactions, which can be comprised of hydrogen bonding, ionic association, ionic bonding, hydrophobic interaction, cross-linking by crystalline segments, and/or solvent complexation.

The term "polyacid" means molecules comprising subunits having dissociable acidic groups.

The term "polyalkylene oxide" ("PO") means non-ionic polymers comprising alkylene oxide monomers. Examples of polyalkylene oxides include polyethylene oxide (PEO), polypropylene oxide (PPO) and polyethylene glycol (PEG), or block copolymers comprising PO and/or PPO.

The term "polycation" means a polymer containing multiple positively charged moieties. Examples of polycations include polylysine, polyarginine, and chitosan.

The term "polyethylene glycol" ("PEG") means a non-ionic polyether polymer being composed of ethylene oxide monomers, and having a molecular weight in the range of about 200 daltons ("d") to about 5000 daltons.

The term "polyethylene oxide" ("PEO") means the non-ionic polyether polymer composed of ethylene oxide monomers. The molecular weight of PEO as used herein is between 5,000 d and 8,000 kilodaltons ("kd").

The term "solids" used with reference to polymer compositions means the total polymer content as a weight percentage of the total weight of the composition.

The term "solids ratio" means the percentage of the total dry polymer contents as a weight percentage of the total solids content.

DETAILED DESCRIPTION

Certain embodiments of the present invention are directed to compositions and methods of augmenting dermal tissues, comprising the step of delivering to the skin, an implantable, bioresorbable association complex of carboxymethyl cellulose (CMC), polyethylene oxide (PEO), and calcium ions. Complexes can generally made by mixing appropriate amounts and compositions of CMC and PEO together in solution, then adding calcium ions to the mixture, and permitting a physical gel to form. When injected into or under the skin, the complex remains at the site for different periods of time, depending upon its composition and location of injection.

Methods for manufacturing compositions are found in U.S. Pat. Nos: 5,906,997, 6,017,301, 6,034,140, 6,133,325, 6,566,345, 6,869,938, and U.S. application Ser. Nos. 10/666, 804, 10/995,448 and 10/371,124. Each of the above patents and applications are incorporated herein fully by reference.

Ionically Cross-Linked CMC/PEO Compositions

Embodiments of the present invention are directed to ionically cross-linked gels Methods for accomplishing these aims comprise the step of delivering to a site, an implantable, bioresorbable composition comprised of CMC, PEO and calcium ions, which are associated with each other by way of ionic bonding, ionic association or ionic crosslinking. Further descriptions of these materials is found in U.S. Pat. No. 6,869,938B1, incorporated fully by reference. We have unexpectedly found that a mixture of CMC, PEO and calcium ions can increase the viscosity of the gel above the viscosity predicted on the basis of either the interactions between the PEO and the calocium, the CMC and PEO, or the CMC and calcium ions. Surprisingly, even with the increased viscosity, dermal fillers can be injected easily into the skin through fine-gauge needles that are typically used for dermal filling. Thus, the compositions of this invention provide advantages not found in previously disclosed compositions for dermal filling. The percentage ratio of CMC to PEO may be from about 10% to about 99% by weight, alternatively between about 50% and about 99%, and in another embodiment about 90% to about 99%. Conversely, the percentage of PEO can be from about 1% to about 90%, alternatively from about 1% to about 50%, and in another embodiment, about 1% to about 10%. In another embodiment, the amount of PE can be about 2.5%. For certain uses, a compositions having 10% PEO, 90% CMC and calcium ions can be desirable.

Gel Structures

The gels of this invention are termed "physical gels." The term physical gels has been used (de Gennes, P. G. *Scaling Concepts in Polymer Physics*. Ithaca, N.Y. Cornell University Press, p, 133, (1979)) to describe non-covalently cross-linked polymer networks. Physical gels are distinguished from "chemical gels" which are covalently cross-linked. Physical gels are relatively weak and have potentially reversible chain-chain interactions which may be comprised of hydrogen bonds, ionic association, hydrophobic interaction, stereo-complex formation, cross-linking by crystalline segments, and/or solvent complexation.

Ionically cross-linked gels can be made by mixing appropriate amounts and compositions of CMC, PEO and calcium ions together in a solution. Additionally, and optionally, the solution can be acidified to promote cross-linking of the polyacid and polyether molecules through hydrogen bonds as described for carboxypolysaccharides and polyethers above and in U.S. Pat. Nos. 5,906,997, 6,017,301, 6,034, 140, 6,133,325, 6,566,345, 6,869,938, U.S. application Ser. Nos. 10/666,804 and 10/995,448 and 10/371,124. Each of the above patents and applications are incorporated herein fully by reference.

Ionically cross-linked gels can be made in the form of a membrane by pouring the solution onto a suitable flat surface, such as a tray, and permitting the mixture to dry to form a membrane at either reduced (for example, >0.01 Torr) or normal (about 760 Torr) atmospheric pressure. Additionally, sponges and microspheres of gel materials can be made. An ionically cross-linked association complex can be placed within the skin or into a structure to be filled.

Although the exact mechanism of ionic cross-linking of CMC/PEO association complex formation is not completely known, one theory is that ionic bonding or association occurs between the acid residues of the CMC and the ether oxygen atoms of the PEO. According to this theory, calcium ions can lie between the acidic residues of the CMC and the ether oxygen atoms of the PEO and can be attracted to valence electrons with the acid and oxygen atoms, thereby forming an ionic bond. Additionally, cross-linking can occur between adjacent CMC molecules, thereby trapping PEO molecules without the necessity for direct CMC/PEO association through ionic interactions.

The above mechanisms for formation of ionically cross-linked association complexes is not necessary to the invention. Our invention does not rely upon any particular theory of the association between the components. Thus, by combining the use of ionic cross-linking and hydrogen bonding, the gels of this invention can be manufactured to have specifically desired properties.

Ionically cross-linked compositions of CMC and PEO require only that the solutions can be handled easily. Dilute solutions (up to about 10% weight/volume) of CMC are easy to handle, and solutions of about 2% CMC are easier to handle. Solutions of PEO up to about 20% (weight/volume) are possible to make and handle, and solutions of about 1% by weight are easy to handle. However, the maximal concentration can be increased if the molecular weight of the PEO is reduced. By way of example only, polyethylene glycol PEG having a molecular weight of about 1000 Daltons can be made in a concentration of about 50%. Further decreasing the molecular weight of the PEO can permit even higher concentrations to be made and handled easily.

Carboxymethyl Cellulose (CMC)

The molecular weight of the CMC can vary from 100 kd to 10,000 kd. CMC in the range of from 600 kd to 1000 kd work well, and CMC of 700 kd works well, and is easily obtained commercially. The degree of substitution (d.s.) can be greater than 0 up to and including 3.

Additionally, substituted CMCs can be useful for embodiments of this invention. CMCs having primary amines, active aldehydes, active tresyl groups, vinyl sulfone groups have been described in U.S. application Ser. No. 10/135,133, published as U.S. 2003/0202970 A1 now U.S. Pat. No. 6,923,961, incorporated herein fully by reference. Such derivatized CPS can have positive charges, negative charges or can have both positive charges and negative charges.

Coascervates may be especially desired in situations in which a long-lasting filler is desired. For example, by using a CMC derivatized to have positive charges along with a CMC having negative charges, an ionically associated coascervate can be formed. These compositions are removed slowly from the body. Methods for derivatizing CMCs can be found in U.S. application Ser. No. 10/135,133 now U.S. Pat. No. 6,923,961, incorporated herein fully by reference.

Polyethylene Oxide (PEO)

Polyethylene oxide (PEO) is a polymer made of repeating ethylene oxide units. Typically, PEOs have molecular weights of greater than about 4000 Daltons. In some embodiment, PEO can have a molecular weight of 8000 kDa. Polyethylene glycol (PEG) is a polymer similar to PEO, except that the numbers of monomer units in the polymer is generally less than for PEO. The MW of PEG suitable for this invention is in the range of about 200 d to about 5 kd, alternatively about 1000 d to 4000 d, and in other embodiments, about 2000 d.

The percentage of CMC to PEO may be from about 10% to about 100% by weight, alternatively between 50% and 90%, and in other embodiments can be about 90% to about 95%. Conversely, the percentage of PEO may be from about 0% to about 90%, alternatively from about 5% to about 50%, and in other embodiments can be about 5% to about 10%.

Once placed at a site, the dermal filler naturally disintegrates and the components are cleared from the body. The time taken to clear the body for certain embodiments is desirably no more than 29 days because of increased regulation by the Food and Drug Administration of devices intended to remain within the body for more than 30 days. However, it can be desirable to provide longer-duration compositions for certain long-term uses. Use of a chemically modified CMC to produce covalently cross-linked materials or use of certain types of dried compositions can decrease the rate of solubilization and therefore can increase tissue residence time.

Ionic Components

The tightness of the association and thus the physical properties of the association complex between the CMC and PEO may be closely regulated by selection of an appropriate amount of calcium ions. The anions accompanying the calcium ions can be of any biocompatible ion. Typically, chloride (Cl) can be used, but also $PO_4^{2-}$, $HPO_3^-$, $CO_3^{2-}$, $HCO_3^-$, $SO_4^{2-}$, borates such as $B_4O_7^{2-}$ and many common anions can be used.

Physical Properties of CMC/PEO/$Ca^{2+}$ Gels

Further increases in cross-linking can decrease measured viscosity (see FIGS. 3 and 4 below). Similarly, for gels containing 1.33% solids, a CMC:PEO ratio of 97:3, and with PEO of molecular weight of 8 kd, and $Ca^{2+}$ have a concentration dependence which has a maximum. However, the maximum for $Ca^{2+}$ is only at around 5% of the total theoretical cross-linking (FIG. 33).

Properties of Ionically Cross-Linked CMC/PEO Compositions

Residence Time and Viscosity of CMC PEO Compositions

For the ionically cross-linked compositions of this invention to be effective as dermal fillers, the material should remain at the site for a sufficiently long time. The time that a composition remains at a tissue site can depend on the ability of the composition to adhere to the tissue, a property termed "bioadhesiveness."

Bioadhesiveness is defined as the attachment of macromolecules to biological tissue. Bioadhesiveness is important in preventing surgical adhesions because the potential barrier must not slip away from the surgical site after being placed there. Both CMC and PEO individually are bioadhesive (e.g., see Bottenberg et al., *J. Pharm. Pharmacol.* 43: 457–464 (1991)). Like other polymers which are known to swell when exposed to water, CMC/PEO gels and membranes are also bioadhesive.

Hydration contributes to bioadhesiveness (Gurney et al, *Biomaterials* 5:336–340 (1984); Chen et al., *Compositions Producing Adhesion Through Hydration, In: Adhesion in Biological Systems*, R. S. Manly (Ed.) Acad. Press N.Y. (1970), Chapter 10). A possible reason for this phenomenon could be that with increased hydration, more charges on the polyacid become exposed, and therefore may be made available to bind to tissue proteins. However, excessive hydration is detrimental to bioadhesion. Thus, a means of controlling the bioadhesiveness of gel compositions and membranes is to control their hydration properties.

Bioadhesiveness can depend on the viscosity of the gel and/or the charge density. A possible mechanism could be that positively charged sites, introduced by way of multi-valentcations or polycations, may interact with negatively charged sites on the tissues. However, other mechanisms may be responsible for the phenomena, and the invention is not limited to any particular theory or mechanism. The gels made according to the invention have unexpected properties which were not anticipated based on prior art. We have unexpectedly found that the addition of polyvalent cations to mixtures of polyacids and polyalkylene oxides can increase the viscosity above that expected on the basis of the CMC and PEO alone. Furthermore, we have unexpectedly found that the addition of PEO to mixtures of CMC and calcium ions and can increase the viscosity above that predicted on the basis of the CMC and calcium ions alone. Additionally, the results are unexpected based on the lack of increase in viscosity of PEO solutions with the addition of calcium ions. This synergism between CMC/PEO and calcium ions can provide a wider range of biophysical properties of the compositions than were previously available.

In addition to altering the ion concentration and valence of the ions of the association complex, increased intermacromolecular association can be achieved using CMC with increased numbers of acid residues. By increasing the numbers or density of acidic residues on the polyacid, there is increasing likelihood of ionic bond formation even at a relatively low pH. The degree of substitution ("d.s") must be greater than 0, i.e., there must be some acid residues available for ionic bond formation. However, the upper limit is theoretically 3 for CMC, wherein for each mole of the saccharide, 3 moles of carboxyl residues can exist. Thus, in the broadest application of the invention for CMC, the d.s. is greater than 0 and up to and including 3. Preferably, the d.s. is between 0.3 and 2. CMCs with d.s. between 0.5 and 1.7 work well, and CMCs with a d.s. of about 0.65–1.45 work well and are commercially available.

The viscosity of a gel can depend on the molecular weight of the CMC. With increased molecular weight, there can be more acidic residues per mole of CMC, and therefore more opportunities for ionic interaction to occur with other molecules in solution. Additionally, the increased molecular weight produces longer CMC chains which can provide greater opportunities for entanglement with nearby polymers. This can lead to a more entangled polymer network. The molecular weights of the CMC can vary from 10 kd to 10,000 kd. CMCs in the range of from 600 kd to 1000 kd work well, and CMCs of 700 kd works well, and is easily obtained commercially.

Resorption of Ionically Cross-Linked Polyacid PEO Compositions

The dermal fillers of the instant invention are intended to have a finite residence time in the body. Once placed at an injection site, the compositions are designed to serve as a filler for a limited time period. Being biodegradable, the dermal filler naturally disintegrates, and the components are cleared from the body.

The degradation and rate of solubilization and disruption of the compositions can be manipulated by careful adjustment of the ionic composition and concentration during formation of the association complexes, by varying the CMC/PEO ratio, and by selecting the appropriate degree of substitution of the CMC and molecular weights of the CMC and PEO. Decreasing the molecular weight of CMC increases its solubility. (Kulicke et al., *Polymer* 37(13): 2723–2731 (1996). The strength of the gel or membrane can be tailored to the surgical application. For example, certain surgical applications (e.g., spine or tendon) may require a stronger, more durable materials than others (such as intraperitoneal applications). Manipulation of the above-mentioned experimental variables allows the manufacture and use of products with variable residence times in the body.

In additional embodiments, emulsions or liposomes containing compositions of this invention can be advantageously used for soft tissue augmentation.

Sterilization of CMC/PEO Compositions

After their manufacture, gels and membranes of this invention can be packaged and sterilized using steam autoclaving, ethylene oxide, γ-radiation, electron beam irradiation or other biocompatible methods. Autoclaving can be carried out using any suitable temperature, pressure and time. For example, a temperature of 250° F. for 20 minutes is suitable for many preparations. For preparations that should not be exposed to water vapor in an autoclave, the compositions, including dried membranes and/or sponges can be irradiated with gamma radiation. In certain embodiments, the intensity of radiation is in the range of about 1 megaRad ("MRad") to about 10 MRad, alternatively, about 2MRad to about 7MRad, in other embodiments about 2.5MRad, or in other embodiments, about 5MRad. Gamma irradiation can be performed using, for example, a device from SteriGenics, Corona, Calif. We observed that sterilization procedures can alter the chemical and physical properties of the compositions and their individual components and thereby can increase the bioresorption of the compositions.

Incorporation of Drugs into Compositions

Ionically cross-linked gels and membranes can be made which incorporate drugs to be delivered to the surgical site. Incorporation of drugs into membranes is described in Schiraldi et al., U.S. Pat. No. 4,713,243. The incorporation may be at either the manufacturing stage or added later but prior to injection. Drugs that are anti-inflammatory, such as aspirin, ibuprofen, ketoprofen, or other, non-steroidal anti-inflammatory drugs can be useful. In certain embodiments, it can be desirable to use drugs or agents that increase formation of new tissues at the site of application. Thus, when used as a dermal filler, as the composition is cleared from the site, new tissue can take its place. Such agents can include fibroblast growth factor (FGF), transforming growth factor-β(TGF-β), platelet-derived growth factor (PDGF) and/or fragments of angiotensin II(A-II). Such fragments include:

```
Asp-Arg-Val-Tyr-Ile-His-Pro-Phe     SEQ ID NO: 1
``` as described in U.S. Pat. No. 6,258,778. This fragment has been shown to be effective in wound healing in the skin.

Additionally, it can be desirable to incorporate anesthetics (e.g., lidocaine and the like), antioxidants (e.g., ascorbic acid, Vitamin E and the like), coenzyme Q, lipoic acid, or other materials. Further, it can be desirable to incorporate replicable vehicles for expression of biologics (e.g., FGF, PDGF, TGF-β, A-II and the like). Such replicable vehicles can comprise a promoter, optionally an enhancer, one or more open reading frames comprising oligonucleotides (DNA or RNA) encoding the biologic, a start codon, a stop codon, and sequences that can target the expressed biologic to the exterior of a cell. Such replicable vehicles can be introduced into a cell adapted to replicate the vehicle and/or express the biologic. Once expressed, the biologic can be secreted or otherwise exposed to cells nearby to promote regrowth of new tissue at the site. In certain of these embodiments, a replicable vehicle can be adapted to be replicated in both bacteria (e.g., *E. coli*) or in eukaryotic cells.

Any drug or other agent which is compatible with the compositions and methods of manufacture may be used with the present invention.

Uses of CMC/PEO/Calcium Compositions as Dermal Fillers

The types of dermal filling using the instant invention is not limited. Examples of dermal uses include injection into the skin (dermal or subdermal), injection under the skin or implantation under the skin. In certain embodiments, a gel composition can be injected through a fine needle (e.g., a 25 gauge, 27 gauge, 29 gauge or 30 gauge) adapted for such uses. In other embodiments, especially wherein a large area of dermis is to be filled, a dried form of a composition can be implanted. For example in excavating injuries or surgeries in which tissue volume is reduced (e.g, removal of a cyst or tumor), a membrane or plug of a composition can be introduced into the affected tissue.

General Methods for Testing and Evaluating Compositions

Hydration Ratio of Dried CMC/PEO Complexes

To determine the rate of hydration and the hydration ratio of a membrane, pieces of dry membranes, about 160 mg each, were placed singly in a glass vial and 20 ml phosphate buffered saline solution (PBS, 10 mM, pH 7.4, Sigma Chemical Company, St. Louis, Mo.) was added. The membranes hydrate, creating soft sheets of hydrogel. After a certain time period (typically 1 hr to 5 days), each of the hydrated membranes was carefully removed from the test vial and placed in a polystyrene petri dish. Excess water was removed using a disposable pipette and by blotting the membrane with tissue paper. Each membrane was then weighed and the hydration ratio (% H) was determined according to the following formula:

$$\% \, H = \frac{(\text{wet mass} - \text{dry mass})}{\text{dry mass}} \times 100\%.$$

Solubility

To determine the solubility of membranes, we measured the relative solubility in water and the aqueous stability of the membranes as a function of their chemical compositions. Membrane solubility in water correlates with the resorption time of the membranes in-vivo.

Typically, the test is performed in conjunction with the hydration measurements outlined above. However, the membranes take up salt during the hydration test due to exposure to PBS. This added salt results in an artifactually high dry weight. Therefore, after determining the hydration ratio, we soaked the membranes in deionized water (30 ml for 30 min.) to remove the salt incorporated in the polymer network. The water was decanted and a fresh 30 ml aliquot of deionized water was added. The membranes were allowed to soak for another 30 min., were taken out of the petri dishes, were blotted dry and were placed in a gravity convection oven at 50° C. to dry.

The drying time was dependent on the amount of water absorbed by the membrane. Highly hydrated, gel-like membranes took up to 24 hours to dry whereas partially hydrated membranes took as little as a few hours to dry. After the membranes lost the excess water, the membranes were allowed to equilibrate at room temperature for 1–2 hours before weighing them. The weight measurements were repeated until a constant weight was obtained. Typically, some rehydration of the membrane took place during this period due to adsorption of moisture from the air.

After the desalinization process described above, the membranes were placed in petri dishes containing 30 ml deionized water to hydrate for periods of from 20 minutes to 5 days. Preliminary studies showed that membranes at pH within the range of 6 and below did not disintegrate during the 1 hr desalinization period.

The solubility (S) of membranes was calculated using the following formula:

$$\% \, S = \frac{(\text{dry mass before soaking} - \text{dry mass after soaking})}{\text{dry mass before PBS soaking}} \times 100\%.$$

The dry mass before soaking is the mass after desalinization, and the dry mass after soaking is the mass after the hydration period in water.

Types of Soft Tissue Dermal Filling

Many types of dermal filling procedures can benefit from the use of the membranes or gels of the present invention. The uses of the present invention are designed (but not limited) to be used to provide increased volume of a tissue that, through disease, injury or congenital property, is less than desired. Compositions can be made to suit a particular purpose, and have desired retention times and physical and/or chemical properties. Depending on the exact formulation (CMC/PEO weight ratio, degree of substitution, degree of polymerization, % total solids, degree of ion association, etc.), the gels according to the invention may vary in consistency from flowable, liquid-like polymer solutions to rigid gels.

Exemplary uses of dermal fillers of this invention can be particularly desirable to fill facial tissue (e.g., nasolabial folds), to increase the volume of the dermis in the lips, nose, around the eyes, the ears and other readily visible tissue. Additionally, dermal fillers can be desirably used to provide bulk to increase the volume of skin secondary to excavating injuries or surgeries. For example, the site around a dermal cyst can be filled to decrease the appearance of a dimple at the site of surgery.

EXAMPLES

The following examples are intended to describe specific embodiments of and are not intended to limit the scope of the invention. Thus, the invention is not limited to these Examples, but can be practiced in any equivalent fashion without departing from the invention.

Example 1

Viscosity of Hydrogels

Because the antiadhesion properties of a hydrogel are dependent upon its viscosity, we determined the relationship between casting solution pH and the viscosity of the hydrogel. We determined the viscosity of PCS/PE solutions at 22° C. using a Brookfield™ viscometer. Using methods published in the brochure *Cellulose Gum*, Hercules, Inc., Wilmington, Del., (1986), page 28. Briefly, the composition of the solution to be tested is selected, and by referring to Table XI on page 29 of Cellulose Gum, the spindle number and spindle revolution speed is selected. Viscosity measurements are made within 2 hr after stirring the solution. After placing the spindle in contact with the solution, and permitting the spindle to rotate for 3 minutes, the viscosity measurement is read directly in centipoise on a Brookfield Digital Viscometer (Model DV-II). We studied 65% CMC/ 35% PEO solutions made with 7HF PH CMC and 1000 kd PEO at a pH of 7.5. Another 65% CMC/35% PEO solution was made at a pH of 3.1.

TABLE 1

Effect of Casting Solution pH on Hydrogel Viscosity

| RPM | Viscosity @ pH 7.5, 22° C. (centipoise) | Viscosity @ pH 3.1, 22° C. (centipoise) |
| --- | --- | --- |
| 0.5 | 38,000 | 13,000 |
| 1.0 | 31,000 | 12,000 |
| 2.0 | 23,200 | 10,400 |
| 5.0 | 19,400 | 8,800 |
| 10 | 15,500 | 7,300 |

Table 1 shows the change in viscosity due to acidification of casting solutions. Reducing the pH from 7.5 to 3.1 decreased the viscosity of the casting solution by more than half. Because the viscosity of a hydrogel is related to its ability to prevent adhesions, possibly due to its ability to remain in one site for a longer time period, gels of higher pH have greater anti-adhesion properties. Further, it is also possible to characterize casting solutions by their viscosity as well as their pH. Thus, for situations in which the measurement of pH is not be as easy or reliable, measurements of viscosity are preferred. To make membranes, the acidified casting solutions containing the weakly H-bonded intermolecular PEO-CMC complex were next poured into polystyrene dishes and dried out in a similar way as described in Example 1. After drying, physical properties were determined.

Example 2

Intracutaneous Reactivity of CMC/PEO Films

Introduction:

The purpose of this test was to evaluate the potential of the test material to produce irritation following intracutaneous injections into rabbits.

Methods:

1. Animals:

As in the previous examples, New Zealand White rabbits were used for this study. The rabbit is the species required by the current version of the International Organization for Standardization. They were obtained from Grimaud Farms of California, Stockton, Calif. Three adult female animals were used, and weighed between 2.2 and 2.3 kg each. The animals were housed individually and maintained at 16–22° C. and 50±20% relative humidity. They were fed Laboratory Rabbit Diet (approximately 200 grams per day) and water ad libitum and had a light:dark cycle of 12 hours on–12 hours off.

2. Sample Preparation:

For the SCI extract, a dry sterile glass tube with a screw cap was filled with 20 ml of the appropriate extracting medium. Two gamma-irradiated (2.5MRad) adhesion film samples (both surfaces exposed) measuring 120 cm$^2$ total surface area were cut into pieces then added to the tube. An additional sterile tube was filled with the same volume of medium to serve as a blank. Each sample and blank was extracted at 37° C. for 72 hours. Each extract was vigorously agitated prior to withdrawal of injection doses to ensure even distribution of extracted matter.

3. Injection Protocol:

On the day of the test the fur on the back of each rabbit is removed on both sides of the spinal column. A 0.2 ml portion of one of the sample extracts is injected intracutaneously at each of five sites along one side of the spinal column of each of three rabbits. A 0.2 ml portion of the corresponding blank (saline alone) is injected intracutaneously at five sites along the other side of the spinal column of each of the three rabbits. The injection sites are observed immediately after injection for erythema, eschar formation, edema and necrosis, and scored at 24, 48 and 72 hours.

4. Evaluation of Results:

All of the animals were observed daily for signs of ill health. The injection sites were examined and scored for any tissue reactions, such as erythema, eschar formation, edema and necrosis, at 24, 48 and 72 hours after injection. For each animal, the individual irritation scores for both erythema and edema are added separately for each test extract at each time point and divided by 10 (the total number of observations). A similar assessment is made of the sites injected with the control. A Primary Irritation Score is then obtained for each time point by subtracting the mean irritation scores for the control from that of the test material.

The Primary Irritation Scores of each animal are then added and divided by the total number of animals to obtain the Primary Irritation Index (PII). The primary irritation response to the test material is then determined.

The methods used for these studies are standards in the art, and meet the standards for the NV SOP 16G-43, *Intracutaneous Reactivity Test* (ISO), the AAMI Standards and Recommended Practices, Vol. 4; Biological Evaluation of Medical Devices (1997) pp. 255–256, and USP 23 [1995] pp. 1699–1702. These standards are shown in Tables 2 and 3.

TABLE 2

Classification System for Intracutaneous (Intradermal) Reactions[1]

| | Score |
|---|---|
| Erythema and Eschar Formation | |
| No erythema | 0 |
| Very slight erythema (barely perceptible) | 1 |
| Well-defined erythema | 2 |
| Moderate to severe erythema | 3 |
| Severe erythema (beet-redness) to slight eschar formation (injuries in depth) | 4 |
| Edema Formation | |
| No erythema | 0 |
| Very slight erythema (barely perceptible) | 1 |
| Slight edema (edges of area well defined by definite raising | 2 |
| Moderate edema | 3 |
| Severe edema (raised more than 1 mm and extending beyond area of exposure) | 4 |
| Total Possible Score for Irritation | 8 |

[1]Other adverse changes at the injection sites shall be recorded and reported.

TABLE 3

Primary Irritation Response Categories in Rabbits[2]

| Response Category | Mean Score (PII) |
|---|---|
| Negligible | 0 to 0.4 |
| Slight | 0.5 to 1.9 |
| Moderate | 2 to 4.9 |
| Severe | 5 to 8 |

[2]The primary Irritation Index (PII) is determined by adding the Primary Irritation Scores for each animal and dividing the total score by the number of animals.

Results:

The animals remained healthy throughout the test period. In none of the animals injected with saline were any irritant responses observed. In only 5 of the 15 sites injected with the test material was any erythema observed, and when present, the erythema was very slight, having a score of 1. In no animal was edema observed after injecting the test material. The Primary Irritation Scores and Primary Irritation Indices are shown in Table 4. The Primary Irritation Indices (PII) of the test material extracted in SCI was 0.

TABLE 4

Primary Irritation Scores and Primary Irritation Index (SCI)

| Rabbit Number | Time (hours) | Control Mean | Test Mean | Primary Irritation Score (Test Mean − Control Mean) |
|---|---|---|---|---|
| 1 | 24 | 0 | 0.1 | 0.1 |
|   | 48 | 0 | 0.1 | 0.1 |
|   | 72 | 0 | 0 | 0 |
| 2 | 24 | 0 | 0.1 | 0.1 |
|   | 48 | 0 | 0 | 0 |
|   | 72 | 0 | 0 | 0 |
| 3 | 24 | 0 | 0.2 | 0.2 |
|   | 48 | 0 | 0.2 | 0.2 |
|   | 72 | 0 | 0.1 | 0.1 |
| Primary Irritation Index | | | 0.3 | |
| (9 Primary Irritation Scores/3 animals) | | | | |

Example 3

Effect of the CMC/PEO Compositions on Gross and Histopathology

Introduction:

The purpose of this study was to determine the effect of placement of 10 to 20 times the expected clinical dose of CMC/PEO films of this invention on the gross and microscopic appearance of the liver, kidney, bladder, bowel, abdominal wall, heart, lung and ovaries.

Methods:

1. Animals:

Twelve female New Zealand White rabbits, 2.4–2.7 kg, were purchased and quarantined for at least 2 days prior to use. The rabbits were housed on a 12:12 light:dark cycle with food and water available ad libitum.

2. Materials:

Gamma-irradiated (2.5MRad) CMC/PEO films (55.2 cm$^2$ (10×expected dose) or 110.7 cm$^2$ (20×the expected dose per rabbit) were implanted surgically into the peritoneal cavities of rabbits. The sutures that were used to close the peritoneum and skin is 3-0 coated Dexon II suture (Davis and Geck, Manati, PR).

3. Sidewall Model:

Adhesions were induced using the same methods as described above for Example 21.

4. Evaluation of Findings:

After 7 days, the rabbits were killed. The abdominal organs were evaluated grossly for any lesions. The kidney, spleen, liver, lung, heart, bowel, abdominal wall and ovaries (in addition to any found to have gross lesions) were placed in formalin for preservation and prepared for histopathologic evaluation.

Results:

CMC/PEO films prevented adhesion formation to injured sidewalls. This was consistent with previous studies described in the Examples above, which showed maximal efficacy of this barrier in the sidewall formation model. No gross lesions were noted upon necropsy. Upon microscopic examination of the tissues harvested according to the protocol, no microscopic lesions were noted. In the spleen, macrophages with material ingested were seen in the two groups of animals that received membranes of the invention. This was more pronounced in the animals receiving the higher amounts of films. This reflects a biological clearance mechanism for the CMC/PEO membranes at this postoperative time point.

Example 4

Effects of CMC/PEO Compositions on Abscess Formation in Rats

Introduction:

A host resistance model was used to determine whether implantation of CMC/PEO compositions of this invention, at the same time as bacterial inoculation affected the mortality and abscess formation as a result of the infection. The purpose of this test was to determine if there was an increase risk associated with the use of this product in potentiating infection.

Methods:

1. Animals:

Ninety female Sprague Dawley rats, 175 to 225 gms, were used for this study. Ten rats were used to produce fecal material. Twenty rats were used to assess the $LD_{10}$ and $LD_{50}$ of the new lot of material and sixty rats were used for the safety study. The rats were acclimated at least 2 days prior to surgery. The rats were housed in the USC Vivarium (an AALAC certified/accredited facility) on a 12:12 hour light/dark cycle. Food and water were available ad libitum except in the immediate postoperative interval.

2. Preparation of Gelatin Capsules:

The fecal contents and feces from rats fed hamburger for 2 weeks were collected and mixed 1:1 with sterile peptone yeast glucose broth containing no preservatives (Scott Laboratories) and 10% barium sulfate. The amount of this fecal preparation that caused mortality in 0 to 20% of the rats (25 μl-$LD_{10}$) or 40 to 60% of the rats (75 μl-$LD_{50}$) was determined in 20 rats. The appropriate amount of material was aseptically added to a gelatin capsule (Number 1, Eli Lilly Company). This capsule was then placed in a second larger capsule (Number 00, Eli Lilly Company). This was referred to as a double-walled gelatin capsule. The capsules were prepared 1 week prior to implantation and stored under frozen conditions under quarantine until the day of surgery.

3. Preparation of Film:

A dried composition of CMC and PEO was gamma-irradiated (2.5 Mrad). Subsequently, CMC/PEO films were cut into a 1.5 cm×1.5 cm piece for each rat.

4. Implantation of Gelatin Capsules:

The rats underwent a standardized procedure for laparotomy (intramuscular anesthesia with ketamine/rompum, shaving with animal clippers, betadine scrub, alcohol scrub). A 2 cm incision was then made on the midline. A double-walled gelatin capsule was placed on the right side of the abdomen through the incision. In the control animals, no further treatment was given. In the animal treated with gelatin capsules containing CMC and PEO, the capsule was placed on the left side of the abdomen between the visceral and parietal peritoneum.

Four groups of 15 animals each were studied, two control groups receiving an $LD_{10}$, and an $LD_{50}$, respectively, and two groups receiving $LD_{10}$ or $LD_{50}$ and an implanted device containing CMC and PEO. The abdominal wall and skin were then sutured closed using two layers of 4-0 Ethicon suture. Following surgery, the rats received analgesic for 3 days and observed twice daily for signs of morbidity/mortality.

5. Necropsy:

The rats that died during the 11 day postoperative observation period were necropsied to confirm the presence of an acute bacterial infection. The rats that survived the initial acute infection were killed on day 11 after surgery. Each rat was examined for the presence of any abdominal abscesses palpated through the skin, odor upon opening and splenomegaly. In addition, four areas of the peritoneum were examined for abscess formation. These areas included the liver, abdominal wall, bowel and omentum.

The abscesses were scored at each site as shown in Table 5.

TABLE 5

Abscess Scoring Methods

| Score | Description |
|---|---|
| 0 | No abscess present at the site |
| 0.5 | One very small abscess present at the site |
| 1 | Several small abscesses present at the site |
| 2 | Medium abscess present at the site |
| 3 | Large or several medium abscesses present at the site |
| 4 | One very large or several large abscesses present at the site |

The scoring were conducted in a blinded fashion by two separate observers and the scores recorded.

Results:

Administration of the CMC/PEO material concurrent with the initiation of bacterial peritonitis did not affect the survival of the rats after infection. The results of these studies is shown in Table 6 below. The group receiving an LD50, 9 of 15 survived, and for the group receiving an LD10, 13 of 15 survived.

TABLE 6

Abscess Formation in Control Animals and Animals Receiving CMC/PEO Mixtures

| Group | Liver | Abdominal Wall | Bowel | Omentum | Total |
|---|---|---|---|---|---|
| Control LD50 | 1.66 | 1.22 | 1.55 | 1.77 | 6.22 |
| CMC/PEO LD50 | 0.77 | 1.55 | 1.0 | 2.33 | 5.66 |
| Control LD10 | 0.54 | 1.78 | 0.46 | 0.85 | 3.6 |
| CMC/PEO LD10 | 0.92 | 1.38 | 0.78 | 0.54 | 3.62 |

As shown in Table 6, in general, the animals receiving the higher dose of abscess-causing bacteria had a higher incidence of abscess formation than did animals receiving the lower dose. The CMC/PEO mixture did not cause any change in abscess formation in animals receiving either dose of bacteria.

Example 5

Manufacture of a Calcium 30% Ion-Associated Gel

In one embodiment of an calcium ionically cross-linked gel of this invention, to make a gel having 2% w/v solids ratio and 95% CMC/5% PEO, we measured 9.5 g of dry, powdered CMC (ds=0.82) and mixed it with 0.5 g dry powdered PEO (MW=8,000 d). We then prepared a beaker with 500 ml of deionized water and 3.2 ml of a stock 20.6% w/v solution of $CaCl_2.2H_2O$. The dry powdered CMC/PEO mixture was then added slowly to the beaker containing the iron chloride/water solution while the solution was stirred at high speed. Once the dry components were mixed into the solution, the stirring speed was reduced and the gel was mixed for 30–50 minutes, by which time until homogeneity was achieved.

The osmolality was then adjusted to a physiologically acceptable value of about 300 mmol/kg by adding about 13 ml of a 30% w/v solution of NaCl and further mixing the gel. The gel was then sterilized in an autoclave for 15 minutes at 250° C.

Example 6

Viscosity of CMC/PEO Ion-Associated Gels

After their manufacture, gels were equilibrated at 25° C. in a water bath. Measurement of gel viscosity were made using standard methods. We determined the viscosity of CMC (7HF, 700 kd)/PEO solutions at 25° C. using a viscometer (Brookfield Digital Viscometer; Model DV-II) using guidelines published in the brochure *Cellulose Gum*, Hercules, Inc., Wilmington, Del., page 28 (1986), incorporated herein fully by reference. Briefly, the composition of the solution to be tested is selected, and by referring to Table XI on page 29 of *Cellulose Gum*, the spindle number and spindle revolution speed is selected. Viscosity measurements made on non-autoclaved gels were made within 2 hr after stirring the solution. Viscosity measurements made on autoclaved gels are made after equilibration to 25° C. After placing the spindle in contact with the solution, and permitting the spindle to rotate for 3 minutes, the viscosity measurement is read directly in centipoise.

FIG. 1 is a graph depicting the relationships between CMC/PEO ratio, molecular weight of the PEO, and viscosity for non-autoclaved, 35% $Fe^{3+}$ ion-associated gels. The top three curves represent data obtained for gels having 2.5% total solids content but made with PEOs having different molecular weights as indicated. The bottom curve represents data obtained for gels having 1.5% total solids content.

The viscosities of the gels ranged from about 10,000 centipoise (cps) to about 510,000 cps. Increasing the percentage of CMC increased the viscosity for each type of gel formulation studied, up to a CMC percentage of about 97. For gels having 2.5% solids content, the effects of cross-linking on viscosities were larger than the effects observed for the gels having 1.5% solids content. However, we unexpectedly observed that increasing the CMC content to 100% resulted in a decease in viscosity for all types of gels studied. The maximum viscosity achieved for each type of gel occurred at relatively low PEO weight content, i.e. CMC of about 97% (by weight; or 88% by unit mole ratio). However, as the PEO was eliminated from the gel composition, the viscosity unexpectedly decreased. Thus, by adding PEO to the gel mixture, we found that the viscosity of the gel increased to values above those predicted based on the prior art for either CMC with ions or PEO with ions alone.

Figure 2:
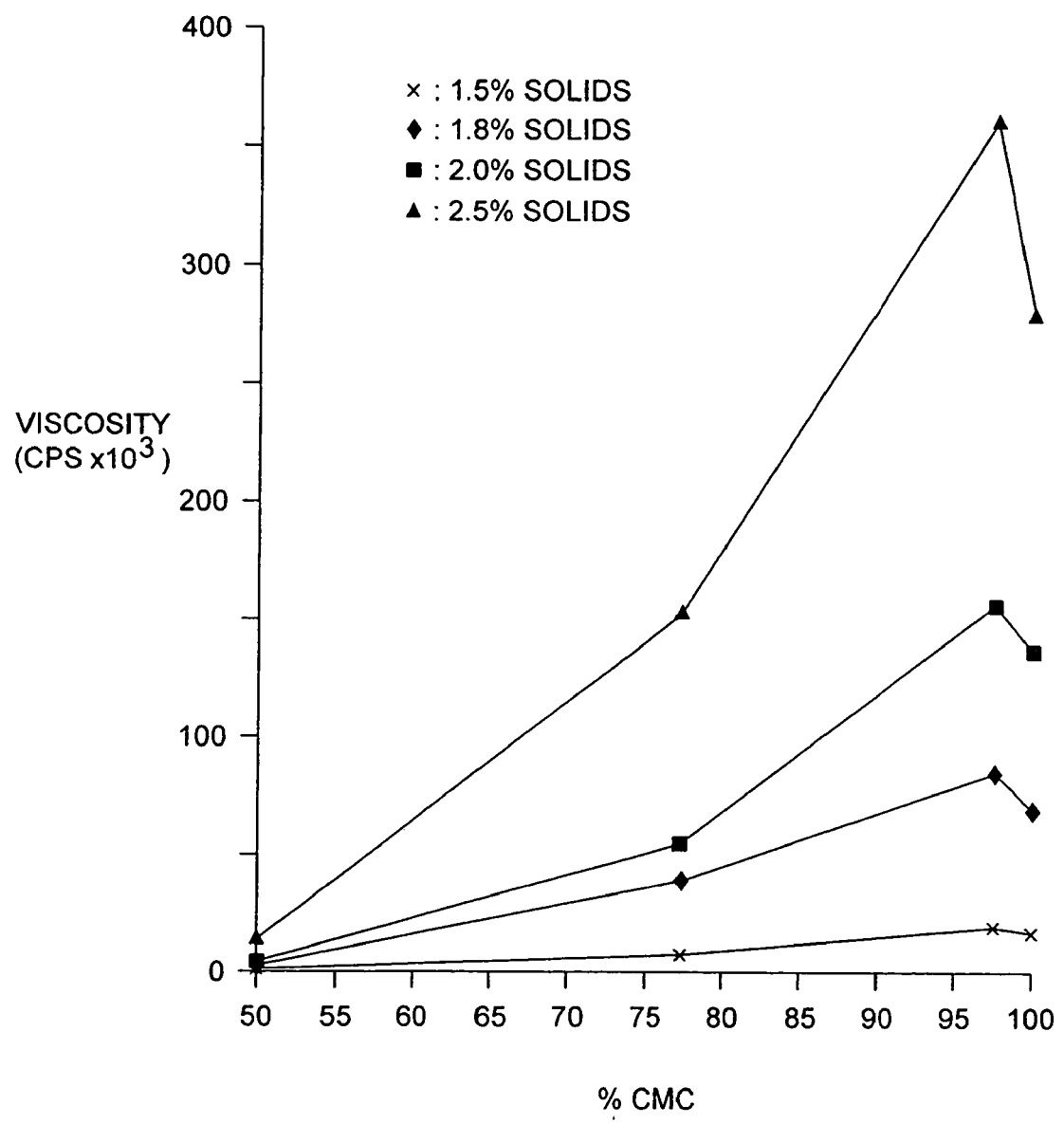
FIG. 2 depicts the relationships between CMC/PEO ratio and percent solids composition and the viscosity of ionically cross-linked gels according to embodiments of this invention.

FIG. 2 depicts a graph of the relationship between the % CMC expressed as a weight percentage of the total solids content in a series of non-autoclaved 35% $Fe^{3+}$ ion-associated gels having different total solids contents, and the viscosity of the gel. The viscosities ranged from less than about 2000 cps to over 350,000 cps. As with FIG. 1, increasing the percent CMC relative to the PEO in the gel increased the viscosity. In general for all compositions of gels studied, increasing the solids contents increased the viscosity. The increase in viscosity was the greatest for the gels having the highest percentage of CMC. However, as observed in FIG. 1, increasing the relative amount of CMC relative to PEO above about 97% CMC unexpectedly decreased the viscosity for gels of each solids composition. As with FIG. 1, a maximal viscosity for each gel composition was observed at a PEO concentration of 2.5% of the total solids contents.

Figure 3:
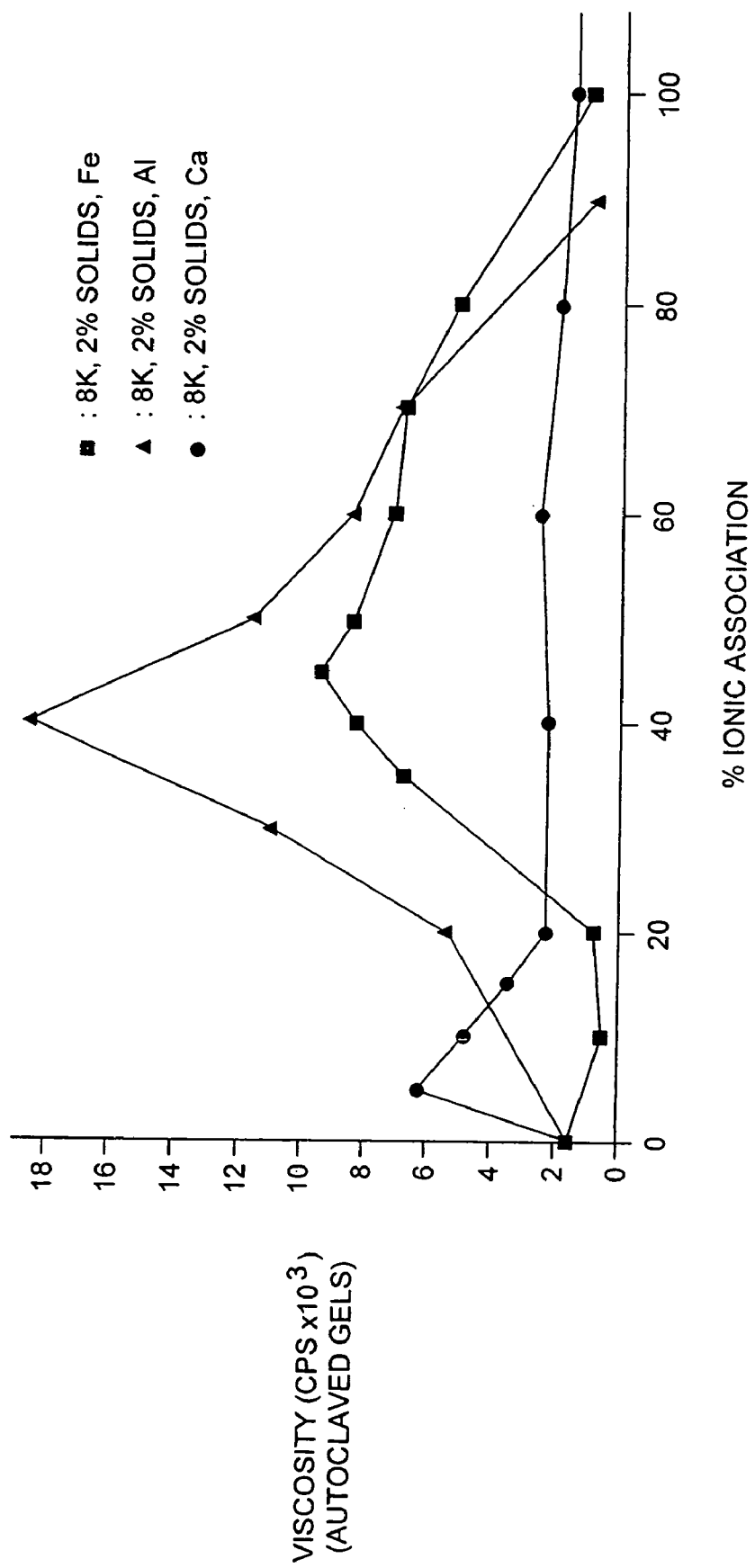
FIG. 3 depicts the relationship between the percent ionic association of CMC/PEO gels, the ionic composition and the viscosity of autoclaved gels of embodiments of this invention.

FIG. 3 depicts a graph of the relationship between calculated % ion-association of autoclaved gels made with 2% total solids, 97% CMC having a degree of substitution of 0.82, and 3% 8 kd PEO, and the measured viscosity of the gels ion-associated by three ions, iron ($Fe^{3+}$), aluminum ($Al^{3+}$) or calcium ($Ca^{2+}$).

For each ion used, relatively broad regions of increased viscosity were observed. In the absence of cations, the measured baseline viscosity was about 1,800 cps. In the lower concentration ranges of ions (relatively low amounts of ion association), as the percent ionic association increased, the viscosity increased until a maximum value was reached. Increasing the percentage of ionic association above that point however, decreased measured viscosity. For $Al^{3+}$ (▲), the viscosity increased from about 1800 cps to about 55,000 cps for ionic association percentages in the ranges of below about 20% and above about 80%. Above about 20% ionic association, the viscosity increased to a maximum observed viscosity of about 180,000 cps observed at about 40%.

For $Fe^{3+}$ (■), the viscosity decreased at values of ionic association of between about 0 and about 20%, to values below about 500 cps. Increasing the amount of ionic association above about 20% increased viscosity to about 60,000 cps for gels having ionic association values in the range of about 35% to about 70%, with a maximum viscosity of about 90,000 cps observed at an association of about 43–45%. Increasing the ionic association further decreased viscosity to about 70,000 cps at an ionic association of about 70%. Further increasing the degree of ionic association decreased viscosity to about 700 cps at 90% association.

For $Ca^{2+}$ (♦) the curve appeared shifted to lower percent ionic association values. A maximum viscosity of about 65,000 cps was observed at the lowest percent association (5%). Increasing the ionic association resulted in decreased viscosity, with a measured viscosity of about 2000 cps observed at ionic association percentages above about 20%.

Regardless of the ion type used, increasing the percent of ionic association increased the measured viscosity up to a certain value of ionic association. However, beyond the maximal values, further increases in ionic association did not further increase viscosity. Rather, the observed viscosity decreased as ion concentration was increased beyond the maximal value. One theory that could account for these observations is that at relatively low ionic concentrations, ionic cross-linking between polymer chains increases as the ion concentration increases. The formation of intra-chain associations reaches a maximum at a certain ion concentration, and at this ion concentration, the viscosity is the highest. However, by increasing the ion concentration to values above that required to produce the highest viscosity can decrease viscosity by promoting intra-chain interactions instead of inter-chain interactions. Intrachain interactions can result in the formation of hairpin loops and other configurations of the reactive groups on the polymer with other groups on the same chain. By forming associations between different portions of the same chain instead of forming intra-chain associations, the higher ion concentrations can keep the individual chains from interacting with nearby polymer chains and can result in decreased viscosity of the gel, compared to the viscosity obtained at an ionic concentration that promotes increased intra-chain interactions. The decreased viscosity with increased ionic association is therefore similar to a "salting-out" effect that can be observed for other polymers in solutions containing ions. However, other theories can account for the observations, and the invention is not intended to be limited to any particular theory.

Figure 4:
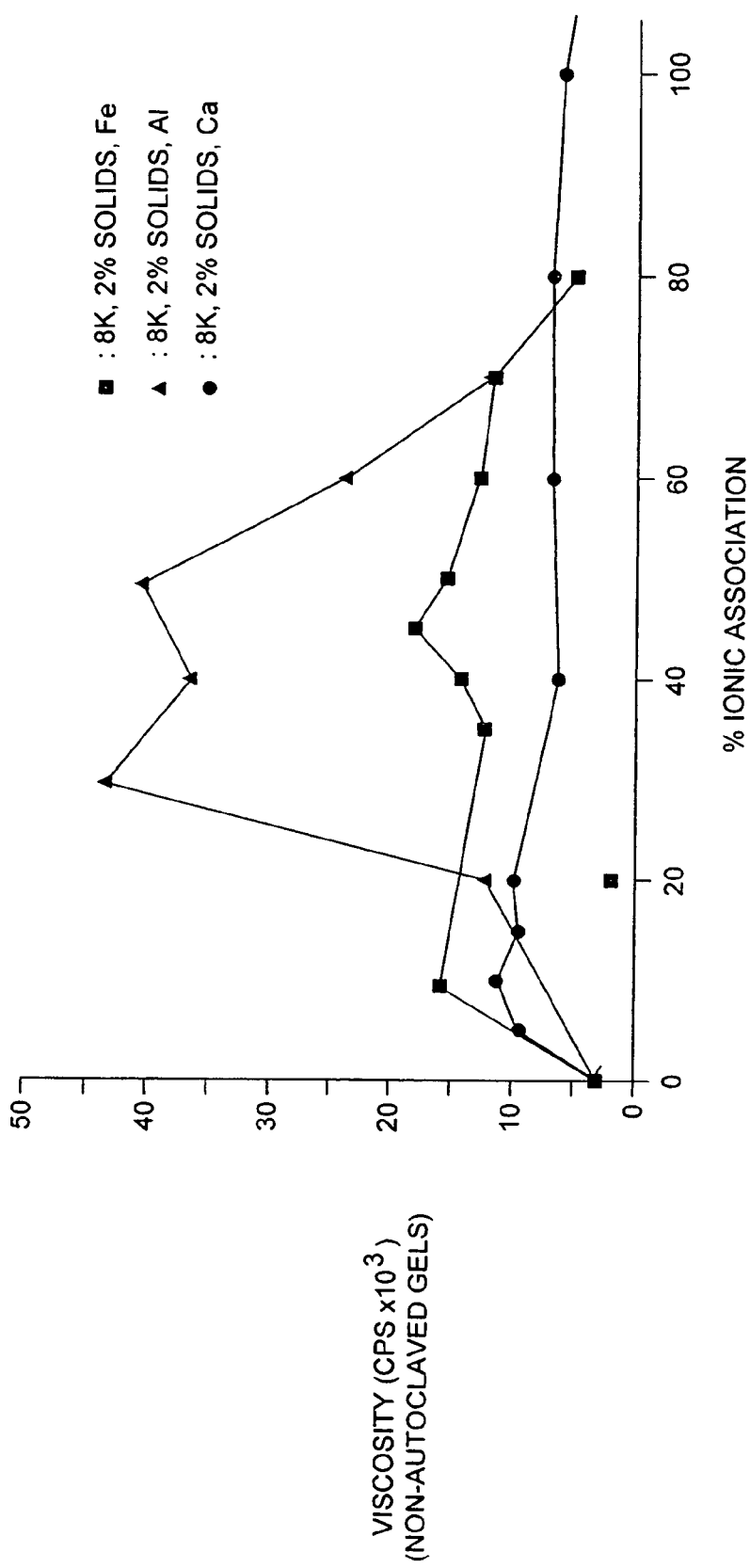
FIG. 4 depicts the relationship between the percent ionic association of CMC/PEO gels, the ionic composition and the viscosity of non-autoclaved gels of embodiments of this invention.

FIG. 4 depicts a graph of the relationship between calculated % ionic association of ionically cross-linked non-autoclaved gels having 2% total solid and, 8 kd PEO and the measured viscosity of the gel for three ions, iron ($Fe^{3+}$), aluminum ($Al^{3+}$) and calcium ($Ca^{2+}$). The non-autoclaved gels generally had higher measured viscosities at each percent ionic association than the autoclaved gels as shown in FIG. 3. Additionally, as with the autoclaved gels depicted in FIG. 3, there were maxima of viscosity at certain percentages of ionic association. In the absence of ionic association, the baseline viscosity of the gels was about 40,000 cps.

For $Al^{3+}$ (▲), the maximum in viscosity appeared as a broad peak of above about 350,000 cps in the range of ionic association of about 30% to about 50%. For $Fe^{3+}$ (■), the viscosity was greater than about 100,000 cps in the range of ionic association percentages from about 10% to about 70%, with peak viscosities of between about 150,000 cps and about 175,000 cps observed at about 10% and about 43–45% ionic association, respectively. For $Ca^{2+}$ (♦), there was an indistinct region of high viscosity at ionic associations in the range of about 10% to about 20%. However, the viscosity was increased above baseline levels for all degrees of ionic association.

Example 7

Manufacture of Ion-Associated Microspheres

Microspheres of ionically cross-linked gels can be made by extruding gel compositions comprising polymers directly into solutions containing multivalent cross-linking ions. The diameters of the microspheres can be determined by the droplet size of the gel during extrusion. For example, Kondo A. *In Liquid Coating Process (Orifice Process)* In: *Microcapsule Processing and Technology* Van Valkenburg, J. W. Ed., Marcel Dekker, N.Y., pp 59–69 (1979), incorporated herein fully by reference, describes different methods for forming droplets of gels. Using smaller orifices, the size of the microspheres can be smaller. Additionally, microspheres can be freeze-dried for use. Freeze dried microspheres comprising ionically cross-linked PA and PO can swell upon exposure to aqueous solutions. As described in U.S. Pat. No. 5,906,997, compositions comprising carboxypolysaccharides and polyethylene ethers can hydrate or swell when placed on a wet tissue, thereby adhering to that tissue. The degree of hydration is related to the degree of bioadhesion, and to the degree of antiadhesion effectiveness. Similar relationships between ion-associated, dried microspheres and antiadhesion properties.

Microspheres can be used for drug delivery into locations in which direct injection of gels is impractical. By way of example, inhalation of an aerosol of microspheres can provide a convenient means for delivering CMC/PEO compositions into the airways. Further, in situations in which it is desirable to deliver a highly viscous gel composition through a fine needle, a suspension of microspheres can be used. A suspension of microspheres can have a viscosity less than that of an equilibrated solution of the same overall composition. This can be because the microspheres can be separated from one another and therefore can have mobility in the suspension. In contrast, a uniform solution of cross-linked gel having the same overall composition can have ionic cross-linking throughout the solution, thereby conferring a higher viscosity upon the solution than is present in the suspension of relatively isolated microspheres.

By using a suspension of microspheres, one can deliver the relatively less viscous suspension through a fine needle or cannula to the desired location without requiring the high pressures needed to force a viscous solution through the same sized needle or cannula. Once injected, the microspheres can swell to form a gel having an overall viscosity less than that of the microspheres, yet greater than that of the injected mixture. Thus, it is possible to provide a greater array of products having desirable viscosities to suit a variety of different applications. For example, for a particularly deep nasolabial fold, such a mixture of microspheres in a solution can be administered using a very fine needle (e.g., 30 gauge), thereby minimizing the size of injection marks. However, once injected, the mixture can attain a high viscosity to provide adequate support for the affected tissue. In the face, large injection marks can be particularly noticable. With the use of a microsphere mixture, the benefits of a high viscosity filler and a small injection mark can be obtained.

Example 8

Manufacture of Ion-Associated Membranes

In other embodiments of this invention, ion-associated gels as described above can be formed into membranes prior to use. In general, dried membranes can have longer residence times in situ than gels that haven't been dried. Methods for manufacturing membranes from casting solutions or gels is described in U.S. Pat. No. 5,906,997, herein incorporated fully by reference. To form membranes of this invention, any of the compositions described herein can be poured onto a flat surface and dried, either at atmospheric pressure (about 760 Torr) or reduced pressure.

Once manufactured, membranes can be used as an adhesion preventative barrier, or can be conditioned prior to use. Membranes made according to this invention can be desirable in situations in which the residence time of the composition at the site is desired to be long.

In yet other embodiments of this invention, a polyacid/polyalkylene oxide membrane can be manufactured according to methods as described in U.S. Pat. No. 5,906,997 and then conditioned by immersing the membrane in a solution comprising a cation or a polycation. By selecting the type of cation or polycation, the concentration of the cation, the time of immersion and other conditions, the cation can penetrate into the surface of the membrane, can associate with charged groups of the polymers in the membrane, and thereby can increase the degree of bonding between the polymers in the membrane. Thus, a membrane surface comprising an ion-associated polymer can be formed. Once so formed, a membrane having a surface conditioning can have increased residence time in the body and therefore can exert antiadhesion effects for periods of time longer than membranes that had not been so treated.

Example 9

Preparation of Dermal Filler I

Dermal filler was prepared by mixing 3.33 g of CMC (Hercules # 7HPH) with 0.37 g of PEO in 100 mL WFI containing 0.601 g of NaCl and 0.255 g of $CaCl_2$ by stirring using a stainless steel blade. The mixed gel was loaded into 1 cc syringes, the syringe was sealed with a tip cap installed on the needle end of the syringe and a plunger installed on the plunger end to contain the gel. The syringe was subject to moist heat to sterilize the gel. This dermal filler (0.05 mL) was injected into the skin of a guinea pig and a histological examination of the injection site after 30 days determined that gel was still present in the lower dermis.

Example 10

Administration of Dermal Filler to Human Skin

A dermal filler was prepared by mixing 3.33 g of CMC (Hercules # 7HPH) with 0.37 g of PEO in 100 mL WFI containing 0.604 g of NaCl by stirring using a stainless steel blade. The mixed gel was loaded into a 1 cc syringe, the syringe was sealed with a tip cap installed on the needle end of the syringe and a plunger installed on the plunger end to contain the gel. The syringe was subject to moist heat to sterilize the gel. The dermal filler was demonstrated to be deliverable through a 30 gauge needle into the nasolabial folds of human skin. Clinical photographs were taken at 1 month and 6 months post injection and demonstrated that the appearance of the nasolabial fold was improved as long as 6 months.

The dermal filler was injected into the glabellar line of a human face and clinical observation indicated that the wrinkle was markedly improved for 3 months. The dermal filler was injected into the left nasaolabial fold of a human face and Restylane, a commercial dermal filler consisting of 2% hyaluronic acid crosslinked with BDDB was injected into the right side of the human face. At three months post injection there was a similar correction on both nasolabial folds. Restylane is prepared by crosslinking and contains particles of crosslinked gel. In contrast the Dermal filler prepared here was smooth and did not contain visible lumps as did the Restylane product.

Example 11

Preparation of Dermal Filler II

A dermal filler was prepared, as in Example 1, by blending two different types of Walocel CMC to achieve the weight ratios shown in Table 7.

TABLE 7

Weight Ratios of Dermal Fillers

| Walocel CRT 20000 | Walocel CRT 30000 | Viscosity after terminal sterilization (Pa-s) |
| --- | --- | --- |
| 100 | 0 | 300 |
| 90 | 10 | 215 |
| 80 | 20 | 205 |
| 0 | 100 | 77 |

The gels were filled into 1 cc syringes and sterilized by moist heat. The viscosity was obtained using a Thermo Haake RS300 rheometer and Rheowin software. The apparent viscosity at 0.1 $sec^{-1}$ was calculated, from a shear rate ramp of 0.1–10 $sec^{-1}$, from the power law values K and n obtained using the Ostwald de Waele model. These dermal fillers were demonstrated to be deliverable through a 30 gauge needle.

Example 12

Use of Dermal Filler in Human Skin

Twelve patients were injected with up to 1.5 mL Dermal Filler on one side and an equal volume of Restylane on the other side of the face in the nasolabial fold. After one month both sides of each face were observed to have a similar clinical correction demonstrating that both dermal fillers were effectively equivalent at one month post injection.

Example 13

Comparison of Different Dermal Fillers

A comparison of the physical properties of several commercial dermal fillers were compared with dermal filler of this invention. Table 8 shows comparisons of dermal fillers of this invention and certain prior art dermal fillers.

TABLE 8

Comparison of Dermal Fillers

| | Crosslinked | Concentration (mg/ml) | Physical Appearance | Viscosity |
|---|---|---|---|---|
| Restylane | yes | 20 | Lumpy | 23300 |
| Juvederm 24 | yes | 24 | Lumpy | 1446 |
| Hylaform | yes | 5.5 | Lumpy | 14500 |
| Dermal Filler of Example 1 | no | 37 | Smooth | 693 |

Example 14

Oxidative Degradation of Dermal Fillers

The oxidative degradation of both HA and CMC was studied by the addition of ascorbic acid. A 4% solution of HA (Lifecore MW 1800 kDa) was prepared in PBS and sodium ascorbate was added to make the concentration 0.02M in ascorbate. A similar solution of 4% CMC (Hercules 7HPH) was also prepared. Both HA and CMC were degraded as measured by a reduction in viscosity. HA was degraded at a rate of 8 times faster than CMC. This result predicts that Dermal fillers prepared with CMC are likely to be more robust that fillers made with HA in terms of being sensitive to oxidation and inflammatory cell produced reactive oxygen or free radicals.

It can be appreciated that other embodiments can be made using the disclosures and teachings of the present invention without undue experimentation and with a reasonable likelihood of success. All such embodiments are considered to be within the scope of this invention.

This application contains Sequence Listing in (1) a computer readable form and (2) diskette. The Sequence Listing is incorporated fully into this application by reference.

All references cited herein are incorporated by reference in their entirety.

We claim:

1. A method for dermal filling, comprising:
providing a composition comprising:
carboxymethyl cellulose (CMC);
polyethylene oxide (PEO);
calcium ions; and
introducing said composition into or under the skin at a site where dermal filling is desired.

2. The method of claim 1, wherein the CMC has a molecular weight in the range of about 10 kd to about 10,000 kd and a degree of substitution of carboxyl residues for hydroxyl residues in the range of greater than about 0 to about 3.

3. The method of claim 1, wherein said PEO has a molecular weight in the range of about 5 kd to about 8000 kd.

4. The method of claim 1, wherein said CMC is in the range of about 10% to about 99% by weight, of the total solids content.

5. The method of claim 1, wherein the CMC is in the range of about 50% by weight to about 99% by weight, of the total solids content.

6. The method of claim 1, wherein the PEO is in the range of about 1% by weight to about 90% by weight, of the total solids content.

7. The method of claim 1, wherein the PO is about 2.5% by weight, of the total solids content.

8. The method of claim 1, wherein the total solids content of the gel is in the range of about 1% to about 10%.

9. The method of claim 1, wherein said composition further comprises a drug selected from the group consisting of antithrombogenic drugs, anti-inflammatory drugs, hormones, chemotactic factors, analgesics, growth factors, cytokines, osteogenic factors and anesthetics.

10. The method of claim 1, wherein said composition comprises microspheres of CMC/PEO and calcium ions.

11. The method of claim 1, wherein said composition is dried to form a membrane.

12. The method of claim 1, wherein said composition is further comprises a coascervate comprising a derivatized CMC having positive charges and a CMC having negative charges.

13. The method of claim 1, wherein the dermal filler is injected into the skin.

14. The method of claim 1, wherein the dermal filler is injected underneath the skin.

15. The method of claim 1, wherein said dermal filler is injected into a nasolabial fold.

SEQUENCE LISTING

<160> NUMBER OF SEQ ID NOS: 1

<210> SEQ ID NO 1
<211> LENGTH: 8
<212> TYPE: PRT
<213> ORGANISM: Homo sapiens

<400> SEQUENCE: 1

Asp Arg Val Tyr Ile His Pro Phe
1               5

16. The method of claim 1, wherein said dermal filler is introduced under a depression in the skin.

17. A method for manufacturing a dermal filler, comprising the steps of:
(a) providing a first solution of CMC having a molecular weight below about 500 kd;
(b) providing a second solution of CMC having a molecular weight above about 500 kd;
(c) mixing said solutions obtained in steps (a) and (b);
(d) adding to said mixed solution obtained in step (c) with a solution of PEO; and
(e) adding a solution comprising calcium ions.

18. The method of claim 17, further comprising the step of forming microspheres from said solution obtained in step (e).

* * * * *

UNITED STATES PATENT AND TRADEMARK OFFICE
CERTIFICATE OF CORRECTION

| | |
|---|---|
| PATENT NO. | : 7,192,984 B2 |
| APPLICATION NO. | : 11/189510 |
| DATED | : March 20, 2007 |
| INVENTOR(S) | : Berg et al. |

It is certified that error appears in the above-identified patent and that said Letters Patent is hereby corrected as shown below:

At Column 24, Claim 12, Line 41, delete "is".

Signed and Sealed this

Fifth Day of June, 2007

JON W. DUDAS
*Director of the United States Patent and Trademark Office*

UNITED STATES PATENT AND TRADEMARK OFFICE
CERTIFICATE OF CORRECTION

PATENT NO. : 7,192,984 B2
APPLICATION NO. : 11/189510
DATED : March 20, 2007
INVENTOR(S) : Berg et al.

Page 1 of 1

It is certified that error appears in the above-identified patent and that said Letters Patent is hereby corrected as shown below:

TITLE PAGE, Item (60), to read as follows:

Continuation-in-part of application No. 10/995,448, filed Nov. 23, 2004, which is a continuation of application No. 09/472,110, filed Dec. 27, 1999, now Pat. No. 6,869,938, issued March 22, 2005 which is a continuation-in-part of application No. 09/023,097, filed Feb. 13, 1998, now Pat. No. 6,034,140, issued March 7, 2000, which is a division of application No. 08/877,649, filed Jun. 17, 1997, now Pat. No. 5,906,997, issued May 25, 1999.

At Column 24, Claim 7, Line 26, please correct "PO" to --PEO--.

At Column 24, Claim 12, Line 39, delete --is--.

Signed and Sealed this

Eighteenth Day of March, 2008

JON W. DUDAS
*Director of the United States Patent and Trademark Office*